United States Patent [19]

Lepper et al.

[11] 3,931,259

[45] Jan. 6, 1976

[54] PROCESS FOR THE PREPARATION OF CARBOXYLIC ACIDS

[75] Inventors: Herbert Lepper, Cologne-Mulheim; Werner Stein, Erkrath-Unterbach, both of Germany

[73] Assignee: Henkel & Cie G.m.b.H., Dusseldorf-Holthausen, Germany

[22] Filed: Nov. 19, 1971

[21] Appl. No.: 200,609

[30] Foreign Application Priority Data

Dec. 1, 1970  Germany............................ 2059042

[52] U.S. Cl.............................. 260/413; 260/531 R
[51] Int. Cl.².......................................... C08H 17/36
[58] Field of Search........................ 260/413, 531 R

[56] References Cited
UNITED STATES PATENTS

| | | | |
|---|---|---|---|
| 2,365,290 | 12/1944 | Price et al...................... | 260/413 X |
| 2,585,129 | 2/1952 | Gebhart et al...................... | 260/413 |
| 2,862,942 | 12/1958 | Snyder.................. | 260/413 |
| 3,678,107 | 7/1972 | Yonemitsu et al............. | 260/531 R |
| 3,692,809 | 9/1972 | Wasecheck........................ | 260/413 |

Primary Examiner—Ethel G. Love
Attorney, Agent, or Firm—Hammond & Littell

[57] ABSTRACT

The present invention provides a process for the preparation of carboxylic acids, which comprises reacting relatively long-chain vicinal diols and/or their complete or part esters with lower carboxylic acids with nitric acid having a concentration of at least 65% at temperatures from 40° to 100°C, and recovering said carboxylic acids.

7 Claims, No Drawings

PROCESS FOR THE PREPARATION OF CARBOXYLIC ACIDS

BACKGROUND OF THE INVENTION

The invention relates to a process for the preparation of higher carboxylic acids.

It is known that it is possible to obtain carboxylic acids from petrochemical raw materials by the direct oxidation of olefins with nitric acid. The method of preparation, however, has the disadvantage that the reaction is not easily controlled since during the process isomerizations may take place in the olefin and therefore carboxylic acids of different chain lengths result. In addition the mixtures of carboxylic acids obtained are considerably contaminated with nitrogen containing compounds, especially nitro-compounds, and moreover, are only obtained in moderate yields. Better results are attained when the olefins are first converted into compounds which contain polar groups attached to two adjacent carbon atoms, for example, hydroxy, ether, ester and/or epoxy groups. Such compounds may be converted into carboxylic acids with higher yields in the presence of the usual oxidation catalysts. Transition metals or their compounds, such as salts or oxides, especially vanadium and vanadium compounds, serve as oxidation catalysts. It is detrimental to employ such a method because the presence of the catalyst considerably impedes the preparation and purification of the products, while giving rise to undesirable consecutive reactions. The separation of the catalyst itself necessitates complicated separation methods, for example the insertion of special exchange resins stable to oxidation, and when such resins are used it is also necessary to conduct the reaction at specific pH values.

OBJECTS OF THE INVENTION

It is therefore an object of the present invention to provide an improved process for the preparation of carboxylic acids consisting essentially of the steps of reacting an organic material starting substance selected from the group consisting of (a) an alkane vicinal diol having 6 to 18 carbon atoms having the formula

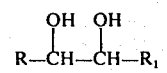

wherein R is alkyl having 4 to 16 carbon atoms and wherein $R_1$ is hydrogen or alkyl having 1 to 12 carbon atoms with the proviso that the total number of carbon atoms in said diol is from 6 to 18 and that when $R_1$ is alkyl at least one of R or $R_1$ has at least 6 carbon atoms, (b) monoesters or diesters of said alkane vicinal diol with lower alkanoic acids, and (c) mixtures of (a) and (b) with nitric acid having a concentration of at least 65% at temperatures from 40° to 100°C to produce said carboxylic acids; and recovering said carboxylic acids.

It is another object of the present invention to provide an improved process for the preparation of carboxylic acids consisting essentially of the steps of reacting an organic material starting substance selected from the group consisting of (a) an alkane vicinal diol having 6 to 18 carbon atoms having the formula

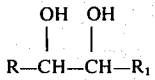

wherein R is alkyl having 4 to 16 carbon atoms and wherein $R_1$ is hydrogen or alkyl having 1 to 12 carbon atoms with the proviso that the total number of carbon atoms in said diol is from 6 to 18 and that when $R_1$ is alkyl at least one of R or $R_1$ has at least 6 carbon atoms, (b) monoesters or diesters of said alkane vicinal diol with lower alkanoic acids, and (c) mixtures of (a) and (b) with nitric acid having a concentration of at least 65% at temperatures from 40° to 100°C to produce said carboxylic acids; dissolving the unreacted starting substance and the formed carboxylic acids in an inert organic solvent to produce an organic solution; extracting the carboxylic acids from the organic solution with a dilute aqueous solution of a strong base; isolating the base-extracted carboxylic acid by acidification with a dilute strong acid; and again reacting said unreacted starting material with said nitric acid.

Other and further objects of the present invention will become apparent as the description thereof proceeds.

DESCRIPTION OF THE INVENTION

It has now been surprisingly found that even without the use of catalysts, relatively long-chain vicinal diols and/or their esters with lower alkanoic acids can be oxidized to alkanoic acids in high yields when the method described below is used.

The new process is characterized by reacting relatively long-chain vicinal diols having 6 to 18 carbon atoms and/or their esters with lower alkanoic acids with nitric acid, having a concentration of at least 65%, preferably 70% to 85%, at temperatures from 40°C to about 100°C, in the absence of oxidation catalysts.

The present invention provides a process for the preparation of carboxylic acids consisting essentially of the steps of reacting an organic material starting substance selected from the group consisting of (a) an alkane vicinal diol having 6 to 18 carbon atoms having the formula

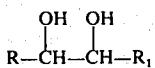

wherein R is alkyl having 4 to 16 carbon atoms and wherein $R_1$ is hydrogen or alkyl having 1 to 12 carbon atoms with the proviso that the total number of carbon atoms in said diol is from 6 to 18 and that when $R_1$ is alkyl at least one of R or $R_1$ has at least 6 carbon atoms, (b) monoesters or diesters of said alkane vicinal diol with lower alkanoic acids, and (c) mixtures of (a) and (b) with nitric acid having a concentration of at least 65% at temperatures from 40° to 100°C to produce said carboxylic acids; and recovering said carboxylic acids.

This discovery was all the more unexpected since it is known from the literature "Chimia 22, 307 (1968)" that in the reaction of vicinal cyclic diols, for example, 1,2-cyclohexanediol, by oxidation with nitric acid in the absence of oxidation catalysts, a complete breakdown of the starting substance to oxalic acid takes place. Further, it was to be expected that nitration reactions would be encouraged by the use of highly concentrated nitric acid, so that products with a high nitrogen content would result.

The limits for the reaction temperatures are given because temperatures below 40°C cause too long reaction times and would therefore make the process uneconomical, whereas at reaction temperatures over 100°C side reactions take place to a greater extent, which reduce the yield of alkanoic acid with breaking down of the carbon chain. It is particularly favorable to carry out the reaction at temperatures between 60°C and 80°C. Such a method of operation is accordingly preferred.

Terminal or non-terminal vicinal diols and/or their part esters with lower alkanoic acids may be used as starting substances, the esters being preferably those derived from formic or acetic acid. When terminal diols or their esters are used as starting substances, alkanoic acids result which have 1 or 2 carbon atoms less than the starting material, since during the nitric acid oxidation, fission of the $C_2$-$C_3$-linkage may also take place besides a fission of the $C_1$-$C_2$ linkage. When non-terminal compounds are used, alkanoic acids are obtained of which the number of carbon atoms corresponds to the number of carbon atoms in the pieces formed by fission of the diol group or is less than this by 1. In the case when alkanoic acids with at least 5 carbon atoms are to be prepared, the vicinal diols or their esters used as starting substances must accordingly have at least 6 or 7 carbon atoms with terminal hydroxyl or ester groups and at least 6 carbon atoms in at least one residue adjacent to the diol or ester groupings with non-terminal hydroxyl or ester groups. Examples of such starting substances are: Hexanediol-1,2, heptanediol-1,2, decanediol-1,2, octadecanediol-1,2, octadecanediol-9,10, hexadecanediol-8,9 or their complete or part esters with lower alkanoic acids, especially formic or acetic acids.

The diols or diol-esters to be used as starting substances may also be present in admixture with one another or in admixture with substances which are inert towards nitric acid under the reaction conditions, for example, paraffin hydrocarbons.

The starting substances are easily obtainable from olefinic petrochemical raw materials, for example through the known hydroxylation reaction, in which case a purification of the products resulting from this reaction may be omitted.

A preferred form of the process according to the invention consists in the use as starting substances of mixtures of substances which have been obtained by hydroxylation of relatively long-chain olefins by means of peracetic acid, acetic acid/$H_2O_2$ or formic acid/$H_2O_2$ mixtures and separation of excess solvent.

Such mixtures of substances may be reaction products of terminal or non-terminal, straight or branched-chain olefins, especially reaction products of so-called central olefins, such as are obtained by catalytic dimerisation of α-olefins of the same or different chain lengths.

On carrying out the process according to the invention the relative proportions of starting substances and nitric acid may vary within wide limits, but the molar ratio should be from 1:6 to 1:60 with the upper limit of 1:60 for the molar ratio being determined principally on economic grounds. It is to be seen as a particular advantage of the process of the invention, however, that relatively large excesses of nitric acid must not be used. A preferred embodiment is one in which the molar ratio of diol (or diol-ester) : nitric acid lies in the range from 1 : 10 to 1 : 20.

The reaction is usually carried out in a heterogeneous phase, i.e. without use of solvents. In some cases it may be desirable to add a solvent, in which the nitric acid is also soluble, for example for the purpose of reducing the viscosity of the reaction mixture. In this case all solvents may be used which do not react with nitric acid under the reaction conditions, and the boiling point of which lies at least 40° C above the reaction temperature used. Suitable solvents comprise: aliphatic or cyclic saturated hydrocarbons, especially decane and mixtures of paraffins, and also polar solvents such as, expecially, alkanoic acids, which here include both lower aliphatic carboxylic acids, for example acetic acid, propionic acid, or butyric acid, and also in certain cases those alkanoic acids which are to be prepared in the process. Further, nitrohydrocarbons, such as nitropropane, can also be used.

The presence of a solvent has no effect on the reaction, i.e. the yields of alkanoic acids are the same with both methods. It is therefore generally preferred to carry out the reaction in the absence of a solvent, since this means that the working up is considerably simplified.

The reaction may be carried out by slowly adding the diol, which may also be present in solid form, to the requisite amount of nitric acid, which has been heated to the desired reaction temperature. After the end of the addition, the reaction mixture is kept for some time at an elevated temperature.

To purify the reaction mixture and recover the final product, the organic constituents are dissolved in a suitable solvent and the organic solution of the alkanoic acids formed is extracted with aqueous NaOH, the concentration of which should be about 10 to 20%. The alkanoic acids may be isolated from the alkali extracts by acidification with dilute sulfuric acid.

The unsaponifiable fractions of the reaction mixture obtained from the organic phase by concentration may be converted for the most part into the alkanoic acids formed in the initial reaction by repeated reaction with nitric acid under the same reaction conditions, so that the total yield of alkanoic acids, referred to diol used, is almost quantitative.

The nitrogen oxides NO and $NO_2$ formed during the reaction may be reacted by oxidation in presence of water to reform nitric acid. This regeneration is suitably carried out by passing the nitrogen oxides together with air into the nitric acid separated from the reaction mixture of the previous batch.

The process according to the invention may also be carried out continuously.

The alkanoic acids obtainable in the process according to the invention have a high degree of purity, i.e. their nitrogen content generally is less than 0.1%.

The invention will be illustrated with reference to the following examples which are not to be deemed limitative of the invention:

EXAMPLE 1

40.4 gm (0.2 mol) of dodecanediol-1,2 in the molten state (m.p. 58°–59°C) were added dropwise from a heated dropping funnel into 220 gm of 80% nitric acid (about 2.8 mol) at a temperature of 60°C with stirring. After the end of the addition, the reaction mixture was maintained for a further 2 hours at the same temperature. After cooling, the organic constituents of the reaction mixture were dissolved in ether and the ethereal solution was extracted several times with 10% aqueous caustic soda to separate the carboxylic acids formed from the unsaponifiable material. The ethereal solution was washed until neutral, dried and concentrated to determine the unsaponifiable matter (12% calculated as unreacted dodecanediol). The alkali extracts were acidified with dilute sulfuric acid and then again extracted with ether, and the ether extracts were freed from traces of nitric acid by washing with water, dried and concentrated. The carboxylic acid mixture obtained, consists chiefly of carboxylic acids having 10 to 11 carbon atoms with a nitrogen content of less than 0.1% and an acid value of 309. The yield, referred to the amount of dodecanediol-1,2 used and calculated as a carboxylic acid having 11 carbon atoms, was 86%.

$HNO_3$ (2.8 mol) at 80°C, and the mixture was stirred for a further 4 hours. After separating the unsaponifiable and unreacted material (5.0 gm = 10%, referred to the material used), 31.0 gm of carboxylic acid were obtained (83% yield calculated as a carboxylic acid having 11 carbon atoms). The nitrogen content of the carboxylic acids was 0.1% with an acid value of 314.

The particular advantages of the invention are that the use of oxidation catalysts can be omitted in the proposed method. Because of this fact, as well as the fact that the working up can be effected in the heterogeneous phase, i.e. in the absence of all solvent, several steps of the process are omitted in the working up of the reaction mixtures.

Examples 2 - 6
The diols listed below were oxidatively decomposed with nitric acid in the same way and under the reaction conditions given.

| Example No. | Starting Compound | Temperature (xx) | Further Reaction Time | $HNO_3$ Concentration | Molar Ratio | N-Content | Yield | Acid Value |
|---|---|---|---|---|---|---|---|---|
| 2 | Dodecane-diol-1,2 | 60/80°C | 1 hr. | 80% | 1:14 | <0.1% | 88% | 312 |
| 3 | Dodecane-diol-1,2 | 80/80°C | 1 hr. | 80% | 1:14 | <0.1% | 85% | 319 |
| 4 | Dodecane-diol-1,2 | 80/60°C | 2 hrs. | 80% | 1:10 | <0.1% | 84% | 317 |
| 5 | Decane-diol-1,2 | 90/60°C | 2 hrs. | 65% | 1:14 | (x) | 80% | 365 |
| 6 | Hexadecane-diol-1,2 | 80/80°C | 2 hrs. | 80% | 1:20 | (x) | 81% | 235 |

(x) under amounts which can be determined.
(xx) second number = temperature of further reaction.

EXAMPLE 7

20.2 gm of the unsaponifiable residues obtained in the oxidative fission of dodecanediol-1,2 with nitric acid were oxidized at 80°C with 2.8 mol of 80% nitric acid. After having been prepared by the method of Example 1, carboxylic acids were obtained with a yield of 72%, calculated as a carboxylic acid having 11 carbon atoms and referred to the material used as dodecanediol-1,2. The nitrogen content of the acid mixture was less than 0.1% and the acid value was 332.

The experiment shows that the unsaponifiable material obtained from preparing the reaction mixtures can be converted for the most part into carboxylic acids by oxidation with nitric acid, so that the total carboxylic acid yield is generally over 90%.

EXAMPLE 8

38.6 gm (0.15 mol) of hexadecanediol-8,9 in the molten state were added dropwise into 134.6 gm of 70% $HNO_3$ (= 1.5 mol) at 80°C in the course of an hour. The mixture was stirred for a further 3 hours at the same temperature. After having been prepared by the method of Example 1, 5.6 gm of unsaponifiable material (15% referred to the diol used) were obtained in addition to 33.8 gm of carboxylic acids (78% yield calculated as octane carboxylic acid). The nitrogen content of the carboxylic acids was 0.1% with an acid value of 383.

EXAMPLE 9

49.6 gm of a mixture of n-dodecanediol-1,2-diformate and n-dodecanediol-1,2-monoformate (average molecular weight 248, saponification value 365), obtained from dodecene-(1) by reaction with $H_2O_2$ and formic acid, were added dropwise into 252 gm of 70%

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A process for the preparation of carboxylic acids consisting essentially of the steps of reacting an organic material starting substance selected from the group consisting of (a) an alkane vicinal diol having 6 to 18 carbon atoms having the formula

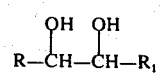

wherein R is alkyl having 4 to 16 carbon atoms and wherein $R_1$ is hydrogen or alkyl having 1 to 12 carbon atoms with the proviso that the total number of carbon atoms in said diol is from 6 to 18 and that when $R_1$ is alkyl at least one of R or $R_1$ has at least 6 carbon atoms, (b) monoesters or diesters of said alkane vicinal diol with lower alkanoic acids, and (c) mixtures of (a) and (b) with nitric acid having a concentration of at least 65% in the absence of an oxidation catalyst at temperatures from 40° to 100°C with the molar ratio of diol or diol ester to nitric acid being from 1:10 to 1:20 to produce said carboxylic acids; and recovering said carboxylic acids.

2. The process as claimed in claim 1 in which the lower alkanoic acid of (b) has 1 to 2 carbon atoms.

3. The process as claimed in claim 1 in which recovering said carboxylic acids consists essentially of the steps dissolving the unreacted starting substance and the formed carboxylic acid in an inert organic solvent to produce an organic solution; extracting the carboxylic acids from the organic solution with a dilute aqueous solution of a strong base; isolating the base extracted carboxylic acids by acidification with a dilute strong acid; and again reacting said unreacted starting material with said nitric acid.

4. The process as claimed in claim 1 in which the nitric acid has a concentration of 70 – 85%.

5. The process as claimed in claim 1 in which the reaction temperature is between 60° and 80°C.

6. The process as claimed in claim 1 in which mixtures of substances are used as starting substances which have been obtained by hydroxylation of relatively long-chain olefins having 6 to 18 carbon atoms by means of an oxidation agent, selected from the group consisting of peracetic acid, acetic acid/$H_2O_2$, formic acid/$H_2O_2$ and the mixtures thereof, followed by separation of excess solvent.

7. The process as claimed in claim 1 in which the reaction is carried out in the presence of a solvent which does not react with nitric acid under the reaction conditions and which has a boiling point of at least 40°C above the reaction temperature used.

* * * * *